US007414709B2

(12) United States Patent
Wagner et al.

(10) Patent No.: US 7,414,709 B2
(45) Date of Patent: Aug. 19, 2008

(54) METHOD AND SYSTEM FOR ONLINE EVALUATION OF GEMSTONES

(75) Inventors: Randall M. Wagner, Mequon, WI (US); Ben L. Wong, Mequon, WI (US)

(73) Assignee: GemEx Systems, Inc., Mequon, WI (US)

( * ) Notice: Subject to any disclaimer, the term of this patent is extended or adjusted under 35 U.S.C. 154(b) by 91 days.

(21) Appl. No.: 11/333,006

(22) Filed: Jan. 17, 2006

(65) Prior Publication Data

US 2006/0164623 A1     Jul. 27, 2006

Related U.S. Application Data

(60) Provisional application No. 60/645,982, filed on Jan. 21, 2005.

(51) Int. Cl.
*G01N 21/87* (2006.01)
(52) U.S. Cl. .................................................. 356/30
(58) Field of Classification Search .................... 356/30
See application file for complete search history.

(56) References Cited

U.S. PATENT DOCUMENTS 5,430,538 A * 7/1995 Kobayashi ................... 356/30

FOREIGN PATENT DOCUMENTS

WO    WO 03/062942 A2 * 1/2002 .................. 356/30

OTHER PUBLICATIONS

Print outs of Sarin website showing and describing its DiaMension tool, DiaVision software and Web Viewer software believed to have been published prior to the filing date of the subject application and possibly as early as 2004.

* cited by examiner

*Primary Examiner*—F. L. Evans
*Assistant Examiner*—Abdullahi Nur
(74) *Attorney, Agent, or Firm*—Jeffrey S. Sokol; Cook & Franke S.C.

(57) ABSTRACT

An online method and system for evaluating a gemstone is provided that enables a consumer to use a personal computer to evaluate the visual appearance and measurement data of the gemstone by emulating the laboratory instruments that previously collected the data for the gemstone. The computer is connected to the internet and a website that is linked to a gemstone database, emulation software and graphical user interface. The consumer identifies the specific gemstone he or she wants to evaluate, and an interactive gemstone certificate screen is displayed. The consumer separately selects and then emulates a variety of lab instruments, such as color and clarity grading, geometric measuring, and light performance and light ray tracing instruments. Graphical images and data pertaining to the selected gemstone are displayed on the computer monitor, and selected portions of the database are downloaded and saved on the computer memory.

23 Claims, 9 Drawing Sheets

METHOD AND SYSTEM FOR ONLINE EVALUATION OF GEMSTONES

This application claims priority on Provisional Application No. 60/645,982 filed Jan. 21, 2005.

TECHNICAL FIELD OF THE INVENTION

This invention pertains to a method and system for evaluating a selected gemstone from a personal computer connected to a website via the internet by emulating the laboratory instruments that previously collected digital data for the selected gemstone.

BACKGROUND OF THE INVENTION

Figure 1:
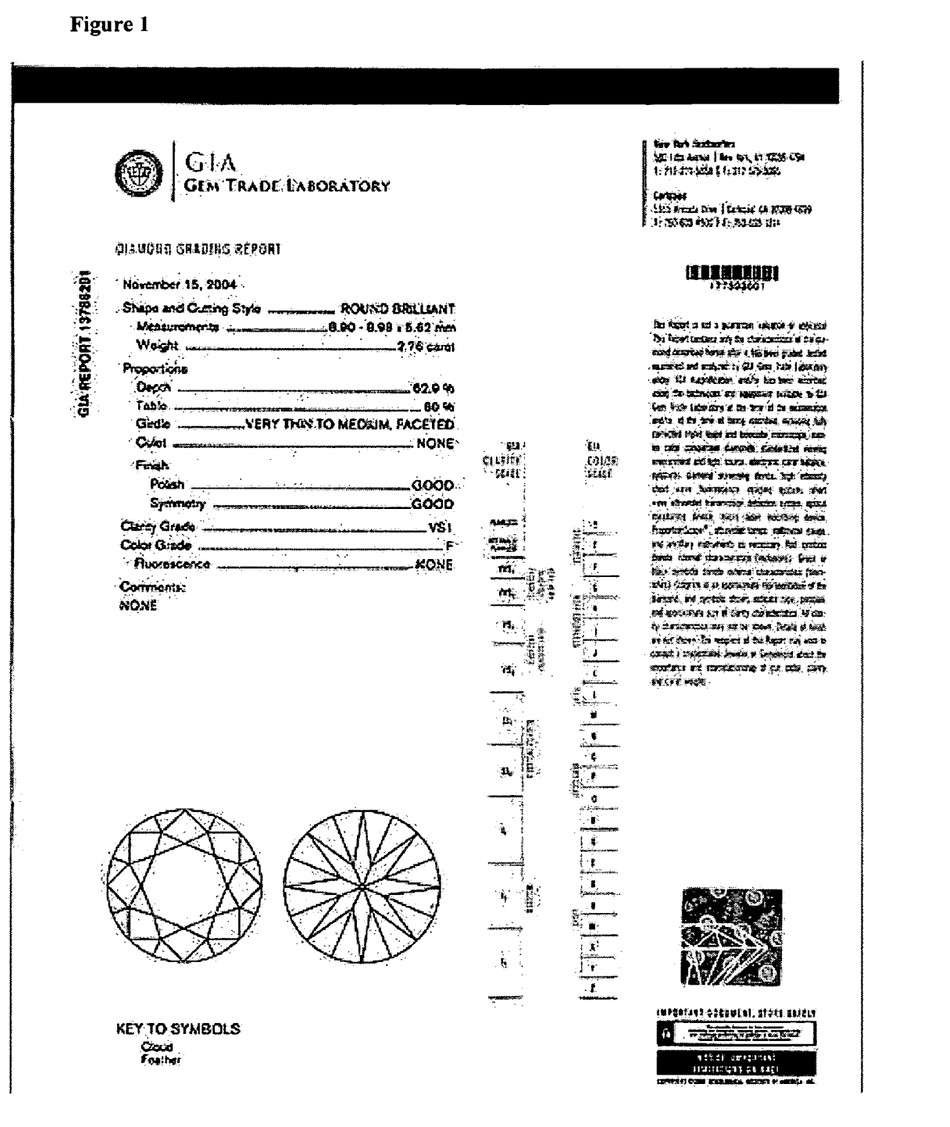
FIG. 1 is a screen printout of a GIA gemstone certificate for a selected diamond.
Figure 2:
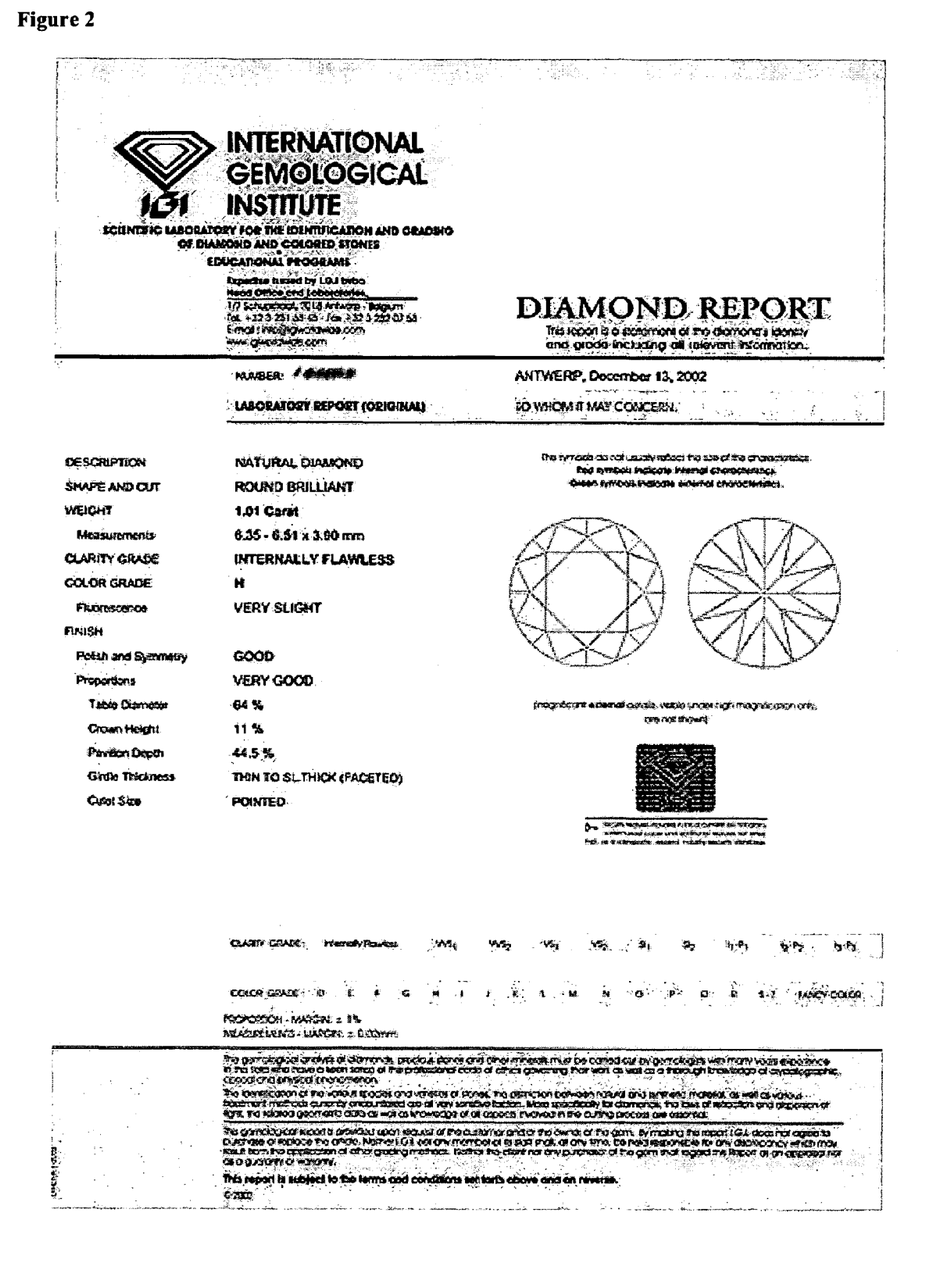
FIG. 2 is a screen printout of an IGI diamond certificate for a selected diamond.
Figure 3:
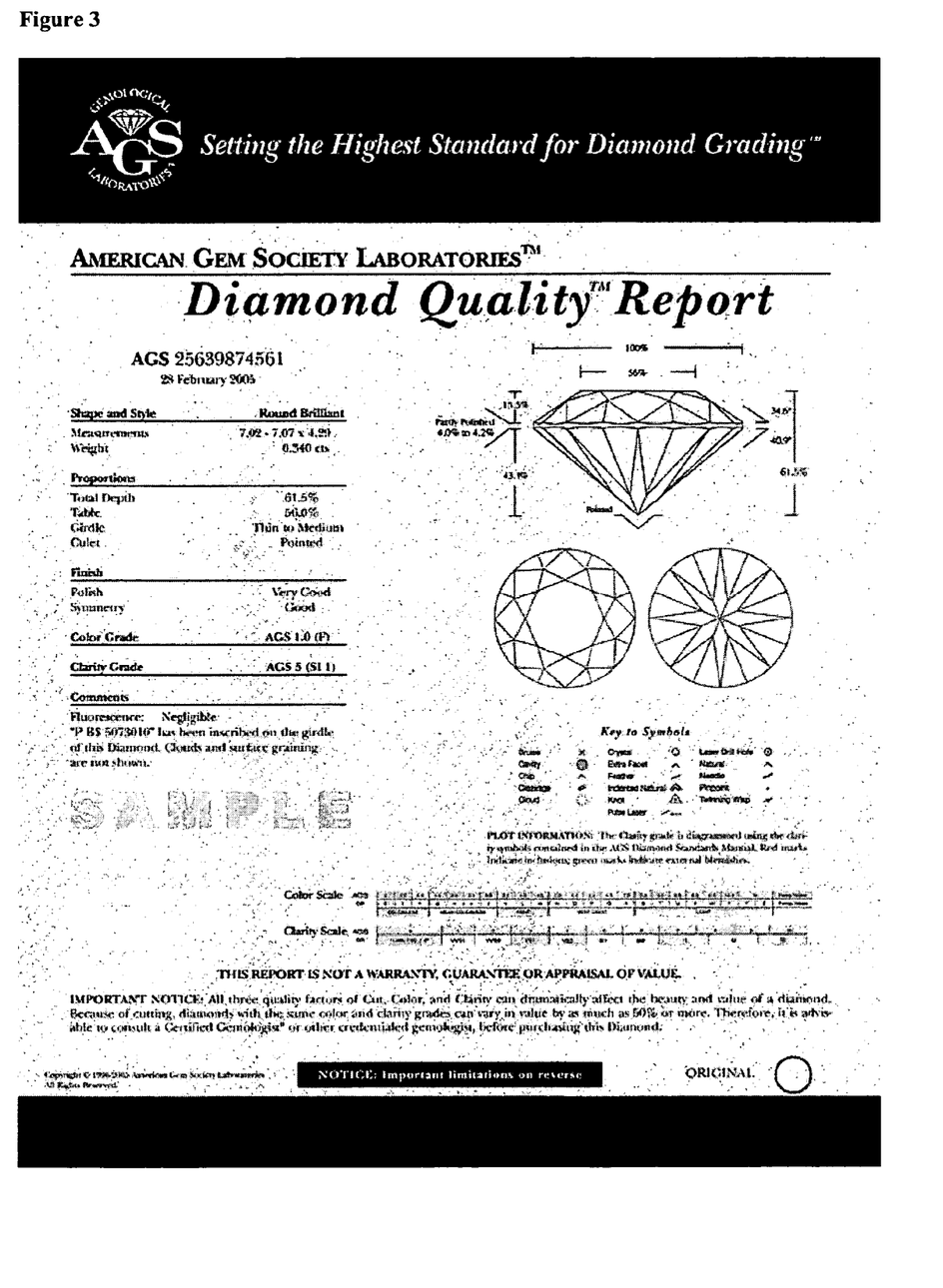
FIG. 3 is a screen printout of an AGS diamond certificate for a selected diamond.
Figure 4:
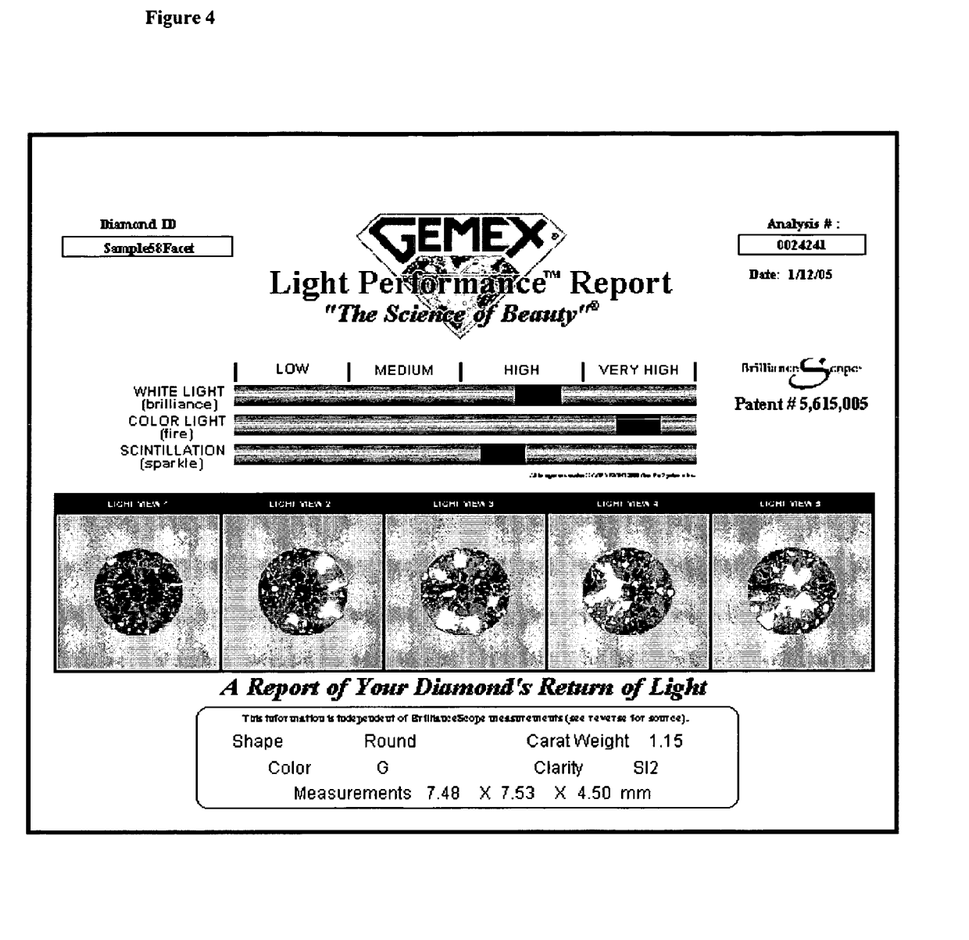
FIG. 4 is a screen printout of a GemEx light performance report.

Like any industry, the diamond and fine gemstone industry is dependent on consumer trust in the quality of the product. In this case, the product is a diamond or gemstone. To increase trust, consumers are given a certificate attesting to the features and quality of their purchase. In the case of diamonds, consumers measure the quality of the diamond by common criteria called the "4C's," or color, clarity, carat, and cut. Generally, the 4C measurements are done by or with the assistance of precision electronic instruments and interpreted by human observation. The results eventually are recorded on a printed document called the "grading certificate," "laboratory report" or "lab report" as shown in FIGS. 1-3. A light performance report may also be printed for a diamond as shown in FIG. 4. These documents are printed on durable paper containing text and two dimensional graphs and/or pictures for the diamond or gemstone. Often the paper documents are converted to an electronic format by scanning or other means for Internet transmission and subsequent viewing on a computer with a display monitor.

Many of the precision instruments used by the gemstone manufacturers and at gemstone testing facilities to make the measurements contained in the grading certificate are capable of producing much more valuable data than is ever reported in the grading certificate. For example, these laboratory instruments include the GemEx BrillianceScope® for analyzing light spectrometry, a Gran Colorimeter® for measuring tint or color, an Ogi Meqa Scope® or Sarin Brilliant Eye® for dimensions and angles, and a Rahman® Spectrophotometer for testing for synthetics. The valuable gemstone data obtained by these instruments is obscured from the consumer for two basic reasons. First, the shear immensity of the data does not allow it to be presented in a printed grading certificate. Second, the diamond sellers believe they need to filter and shape the information presented to the consumer in order to sell the gemstones.

Sophisticated consumers seek out information about gemstones before they make a purchase. Generally, there are two ways for consumers to obtain information about a gemstone they are considering to purchase. First, the consumer can request information from the seller of the gemstone. Second, and more recently, the consumer can do research on their own, primarily via the Internet. Unfortunately, the information available through these two channels closely parallels the same information contained in a traditional grading certificate. In some instances, the consumer is provided some additional text information that is not available on the printed reports, however, the information is very limited and difficult for the consumer to understand.

The present invention is intended to solve these and other problems.

BRIEF DESCRIPTION OF THE INVENTION

This invention pertains to an online method and system for evaluating a gemstone. A consumer uses a personal computer to evaluate the visual appearance and measurement data of the gemstone by emulating the laboratory instruments that previously collected the data for the gemstone. The computer is connected to the internet and a website that is linked to a gemstone database, emulation software and graphical user interface (GUI). The consumer identifies the specific gemstone he or she wants to evaluate, and an interactive gemstone certificate screen is displayed. The consumer separately selects and then emulates a variety of lab instruments, such as color and clarity grading, geometric measuring, and light performance and light ray tracing instruments. Graphical images and data pertaining to the selected gemstone are displayed on the computer monitor, and selected portions of the database are downloaded and saved on the memory of the personal computer.

One advantage of the present invention is the completeness of the information. Consumers are not limited to the printed information on a grading certificate. Instead, consumers use a computer to emulate the laboratory instruments that actually obtained the printed information on the certificate, and information not printed on the certificate. Consumers display visual images produced by the lab instruments, and can manipulate those images as if they were operating the instrument themselves. The consumer has much more complete access to the data obtained by the manufacturer and testing facility when they evaluated the gemstone, which is now being presented to a consumer. Consumers can focus on the characteristics and aspects of the gem or its flaws, and can inquire about any questions or concerns they may have with the seller.

Another advantage of the present invention is the availability of the information. Consumers can conduct their review of a gemstone in the privacy and convenience of their own home, or that of a person they trust. In fact, the present invention applies to portable mediums, such as a CD, PDA, or web-enabled communications device. The consumer need not rely on the tools and advice of the seller to make their purchasing decision. Any question or concern the consumer may have can be more intelligently discussed with the seller.

A further advantage of the present invention is the ease of use. Consumers simply input an identification number for a selected gemstone and view a set of interactive gemstone certificate (IGC) screens that are similar to the paper grading certificates that are presently in use. The IGC has control features that allow the consumer to first select the gemstone from the database to examine, then select the category of data, images and information to examine on the gemstone, then to select, manipulate, and explore specific details over the full range of information, images and data available on that gemstone, in depth, in a way emulating the a measuring devise processes and/or actual instrument processes that were used to create the data. For example, the consumer can rotate the image of the gem, zoom in on an area of interest, and change lighting setting to better view the selected gemstone. The information of concern is obtained by clicking on that piece of information or the use of pull down menus.

A still further advantage of the present invention is that the evaluation information is available for colleting and storing into a unified database. The gemstone image and measurement data was previously obtained by the actual gemstone evaluation instruments. Costs associated with implementing the method and system are kept to a minimum.

Other aspects and advantages of the invention will become apparent upon making reference to the specification, claims and drawings.

DESCRIPTION OF THE PREFERRED EMBODIMENTS

While this invention is susceptible of embodiment in many different forms, the drawings show and the specification describes in detail a preferred embodiment of the invention. It should be understood that the drawings and specification are to be considered an exemplification of the principles of the invention. They are not intended to limit the broad aspects of the invention to the embodiment illustrated.

The invention pertains to a method and system including a software program that interacts with a gemstone database to separately emulate the operation of a number of gemstone evaluation processes and instruments. The database includes gemstone evaluation data for a plurality of individual gemstones. In conjunction with a remote computer terminal such as a personal computer, the user can observe, analyze, and perform virtual measurements on a selected gemstone. Although not limited to the following, the software program includes emulation software programs for emulating the operation of the GemEx BrillianceScope® light performance instrument, a Gran Colorimeter® color grading instrument, a GemEx GemSpec® imaging spectrophotometer, and an Ogi, Mega Scope® or Sarin Brilliant Eye® geometric measuring instrument. The instrument emulations are viewable on any computer display device, including without limitation, a monitor, a touch screen display, web-browser, PDA or web-enabled phone device. The remote computer terminal includes a processor, a monitor and an input device such as a keyboard or mouse. The remote terminal should also include an associated memory and a printer. Although some of the instrument emulations are in color and are best viewed on a color monitor, the broad aspect of the invention is not limited to color or the use of a color monitor.

Figure 5:
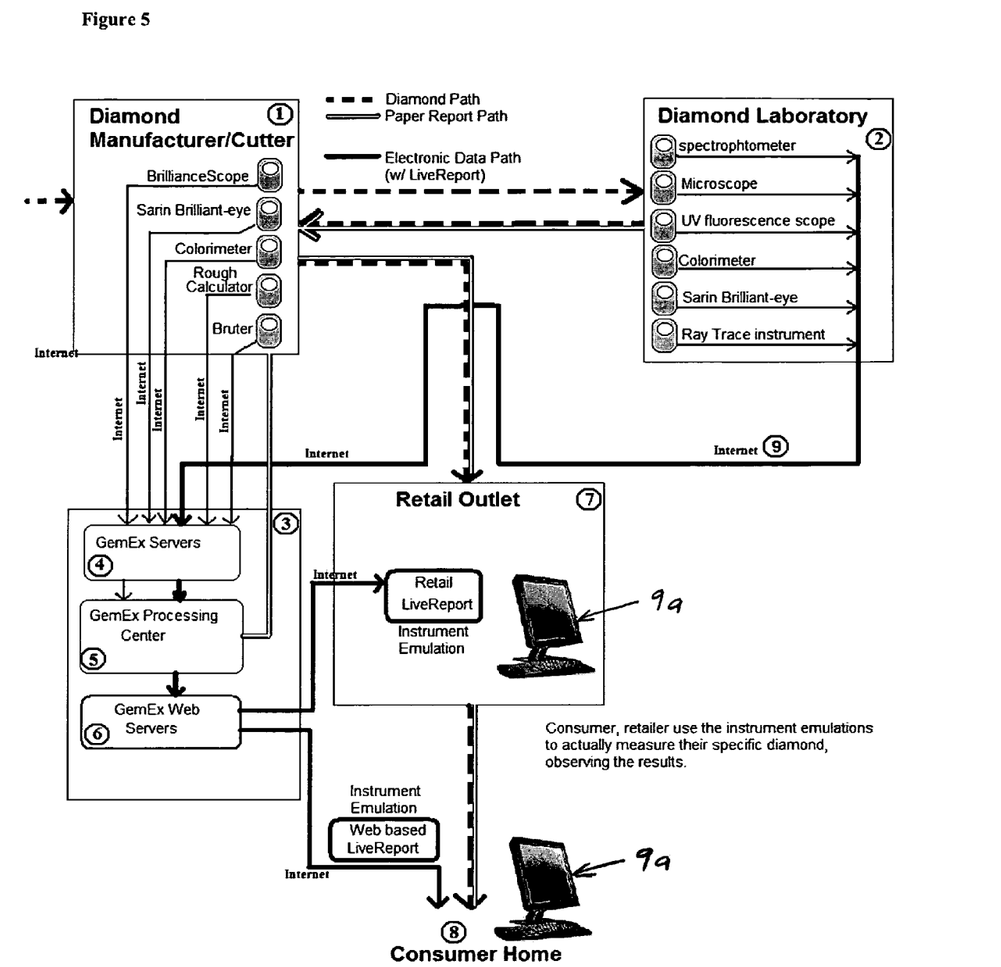
FIG. 5 is a flow chart showing the flow of gemstone data for the present online gemstone evaluation method and system invention.

The gemstone database includes gemstone evaluation data for a multitude of gemstones such as diamonds. The gemstone evaluation data or gemstone data includes text, images and video pertaining to the actual gemstones. The gemstone data is obtained from a number of sources as shown in FIG. 5. These sources of gemstone data or gemstone information include the gemstone or diamond manufacturing plant (1), grading laboratory (2), wholesaler, or other similar locations where gemstone evaluations are made. The facilities perform actual evaluations of the actual gemstones, including tests or measurements on the gemstones. These facilities then transmit or make available the resulting gemstone data to a selected memory or database, such as for a designated computer system (3), via the Internet (9).

The facilities transmit the gemstone data with gemstone identification numbers. The gemstone date for each specific gemstone is matched to or otherwise associated with a corresponding gemstone identification number. In other words, the gemstone data corresponding to a particular gemstone is given or assigned a unique gemstone identification number. The gemstone identification number is part of the gemstone data for a particular gemstone. The gemstone identification number may or may not be the same as any identification number that is physically marked on the actual gemstone, which is sometimes done for diamonds. The gemstone data is received in a data server (4), and is then processed by a processing center (5) and added to the database located on a web server (6). The web server (6) hosts a website accessible to the Internet (9). The web server (6) also hosts the main program and database, which are accessible via the website.

The method and system for evaluating a gemstone can be used by a diamond retailer (7) or an individual consumer (8). Accordingly, the remote terminal (9a) can be located at a retail store (7), or it can be any terminal available to the consumer (8) such as their personal home computer. The user (7, 8) uses the terminal (9a) connected to the Internet (9) to access the website hosted by the server (6). The entry device such as the keyboard or mouse of the terminal (9a) is used by the user (7, 8) to enter a specific diamond identification number for a selected gemstone onto a gemstone identification number entry screen of the website. The main software program then uses the entered gemstone identification number to retrieve the required data, images, and video files from the database for the selected gemstone, and temporarily or permanently stores the gemstone data for the selected gemstone on the associated memory for the local imaging device or monitor of the terminal (9a). The gemstone data for the selected gemstone is then prepared by the main software program to be displayed as an electronic interactive gemstone certificate (30) using the various instrument and process emulators or emulation subprograms of the main software program.

Figure 6:
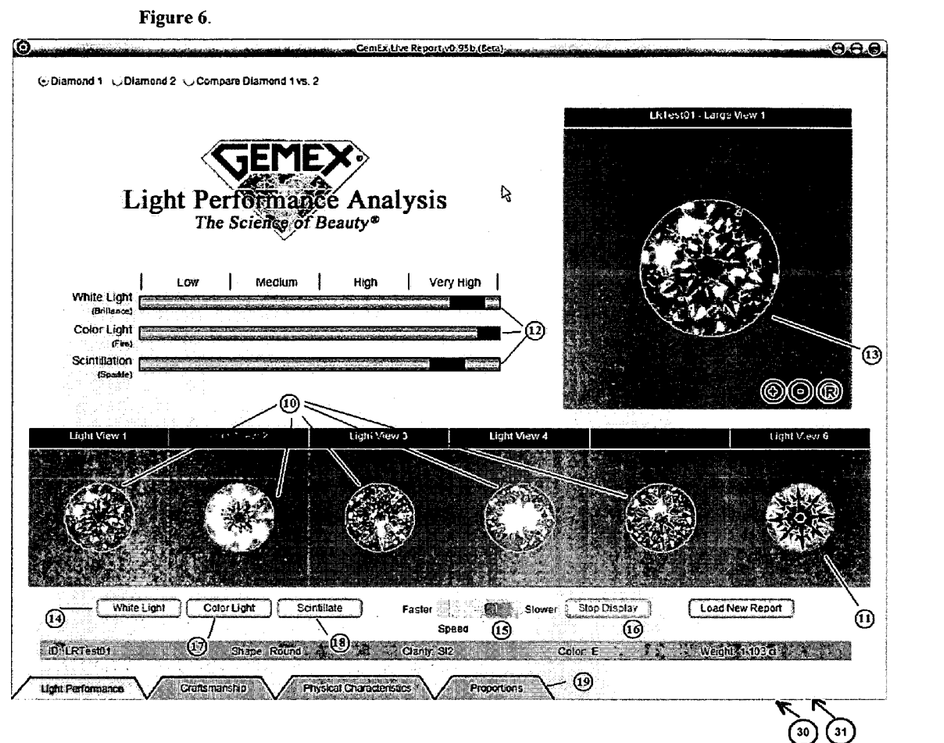
FIG. 6 is a screen printout of a GUI screen for the light performance emulator.

When the main software program and interactive gemstone certificate (30) are initiated, the first screen to come up is the light performance and gemstone identification image emulation screen 31 as shown in FIG. 6. When the gemstone is a diamond, the screen consists of six different images of the diamond, five reflective "light performance" images, one for each reflected light position (10) and one diamond identification image (11). The light performance of a diamond is broken into three different categories; White Light (brilliance), Color Light (fire), and Scintillation (sparkle). The results of each category is displayed on a bar graph (12) comparing the performance of the individual diamond to all other diamonds in the world.

The user (7, 8) can click on any image on screen (31) and it will be shown in the large image window (13) as in FIG. 6. The user can then zoom in on any part of any image by clicking the + or − buttons in the large image window. The user can click on the white light button (14) to see where the White Light is returned in each lighting position. The images for all five reflected light images (10) are then displayed in the large image window (13) on a rotating basis. The speed of rotation is adjusted using the speed bar (15), or alternately the user (7, 8) may stop the display by pressing the stop display button (16) and then examine each white light image in detail. The user can focus on any part of the image and zoom in for more detail. The same process can be repeated for the Color Light return using the Color Light button (17). The scintillation button (18), can be pressed and the entire light return for the diamond can be examined as if the user was holding the diamond in his hand and rocking it back and forth.

The user (7, 8) can also use the light performance screen (31) to examine the diamond identification image (11). (FIG. 6). When this image is clicked on, the diamond identification image appears in the large image window (13). This image, when used with a special hand viewer enables the user to visually confirm the diamond in hand is actually the diamond being examined on screen. The user is able to click on the image and zoom in on any part of the diamond focusing on any part of the unique faceting patterns exhibited by the diamond. The user can select any one of the other tabs (19), to change to other categories, such as "Proportions," "Physical Characteristics" and "Craftsmanship."

Figure 7:
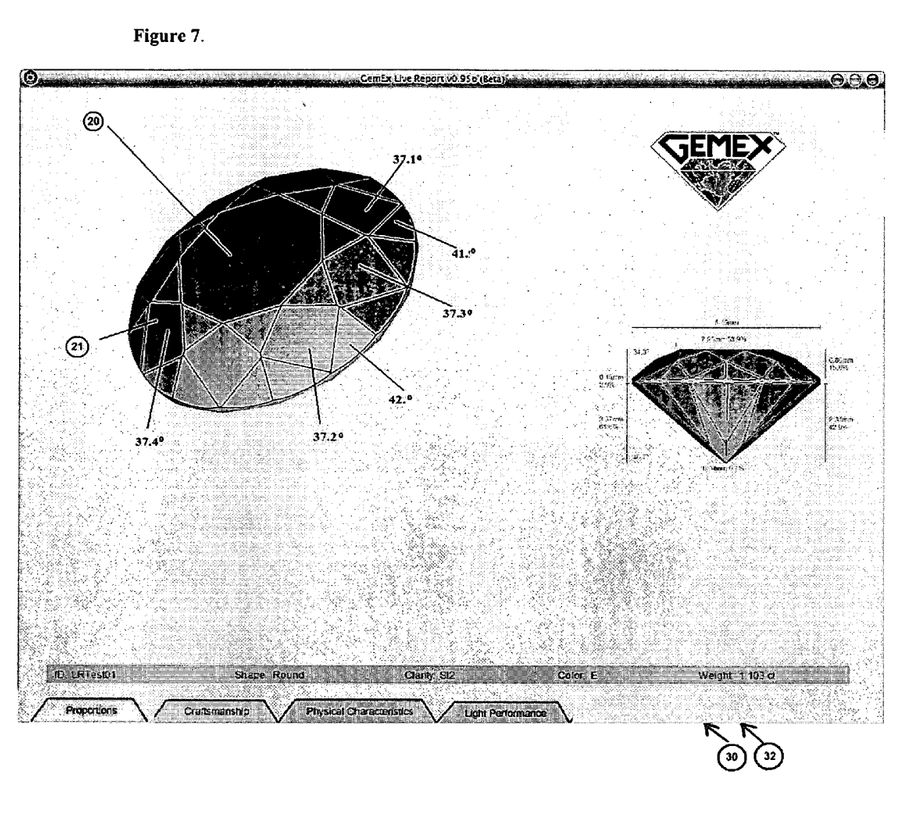
FIG. 7 is a screen printout of a GUI screen for the proportion evaluation emulator.

When the user (7, 8) selects the "Proportions" tab (19), the proportions or geometric measurement emulation screen (32) is presented as shown in FIG. 7. On this screen (32), the user can click on the diamond (20) with the pointer, and then move the mouse, to rotate, flip or twist the diamond in any fashion. The user can then select any facet (21) and the associated angles appear on the screen. All the information that was originally captured using the actual measuring instrument is available upon demand for the user, just as if he was using the instrument itself.

Figure 8:
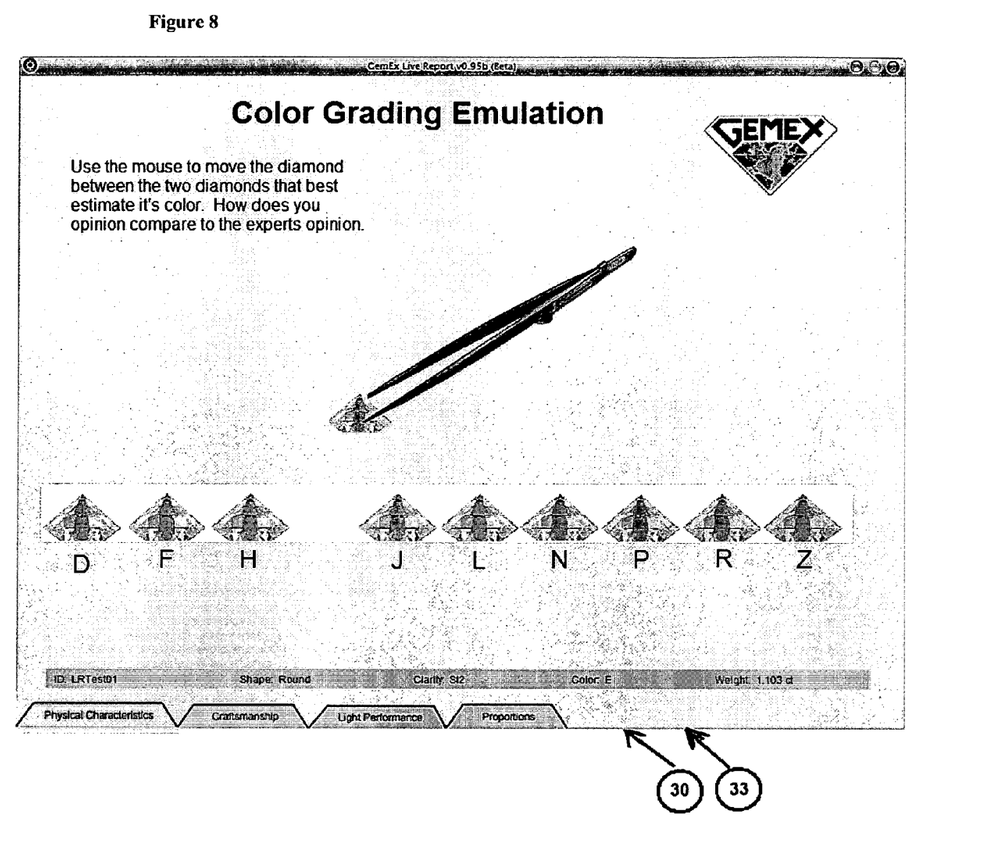
FIG. 8 is a screen printout of a GUI screen for the color grading emulator.
Figure 9:
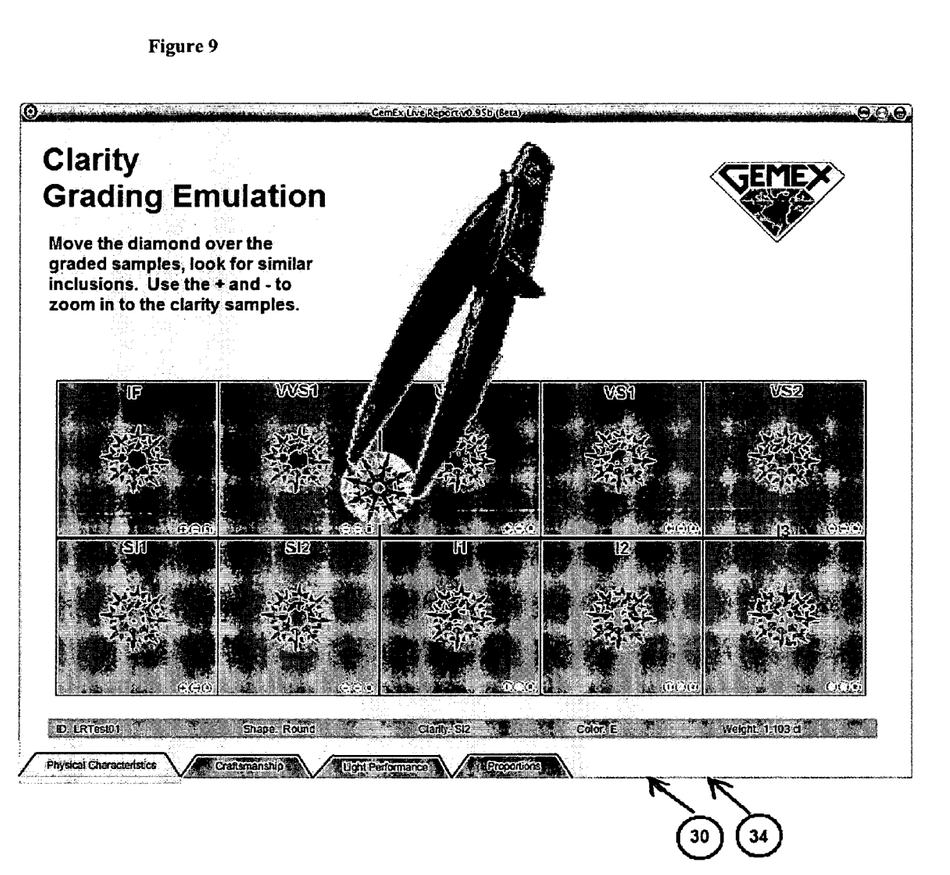
FIG. 9 is a screen printout of a GUI screen for the clarity grading emulator.

When the user (7, 8) selects the "Physical Characteristics" tab (19), he or she is presented with a number of emulators that include the "Color Grading" emulator screen (33) as shown in FIG. 8, and the "Clarity Grading" emulator screen 34 as shown in FIG. 9. On the Color Grading screen (33), the operator (7, 8) takes the diamond and moves it to the various diamond samples. As the diamond is move between any two of the sample diamonds, the sample diamonds separate and allow the user to place the diamond between the two samples to allow examination of the color. The user determines which two samples the diamond should be placed between to determine the correct color grade, just as the original or actual grader does.

A similar procedure is followed on the "Clarity Grading" emulator screen (34) shown in FIG. 9. Typically, there is a single inclusion, the largest or most visible that determine the clarity grade. The user (7, 8) can examine that inclusion and compare it to the many samples provided. The user compares the grade setting inclusion in the subject diamond to the clarity samples shown. For a closer examination, the user can zoom in on any of the samples in addition to enlarging the subject diamond image.

While the invention has been described with reference to a preferred embodiment, it will be understood by those skilled in the art that various changes may be made and equivalents may be substituted without departing from the broader aspects of the invention.

We claim:

1. An online gemstone evaluation method in which a remote terminal with a graphic display and processor is operably connected to the internet to emulate a gemstone light performance evaluation instrument to evaluate a gemstone, the gemstone being selected from a plurality of gemstones; each gemstone having an identification number, and the gemstones being previously evaluated by the gemstone light performance evaluation instrument to obtain actual gemstone light performance image data for the gemstones, said gemstone evaluation method comprising the steps of:

providing a gemstone evaluation website accessible via the internet, said website being readably linked to a database and operably linked to instrument emulation software including light performance instrument emulation software, said instrument emulation software having a corresponding graphic user interface;

storing the actual gemstone light performance image data for the previously evaluated gemstones in said database;

accessing said gemstone evaluation website via the internet and remote terminal;

inputting the identification number for a selected gemstone via the remote terminal; and, using said light performance instrument emulation software via the remote terminal to emulate the operation of the gemstone light performance evaluation instrument and obtain specifically selected portions of the actual gemstone light performance image data for said selected gemstone, said specifically selected portions of the actual gemstone light performance image data being viewable on the remote graphic display.

2. The online gemstone evaluation method of claim 1, and wherein the gemstones are previously evaluated by a plurality of gemstone evaluation instruments to obtain a collection of actual gemstone image data for the gemstones, and the collection of actual gemstone image data is stored in said database, said remote terminal is used to emulate the operation of the gemstone evaluation instruments to obtain specifically selected portions of the collection of actual gemstone image data for said selected gemstone.

3. The online gemstone evaluation method of claim 2, and wherein said database includes a collection of individual images that are manipulatable via the remote terminal.

4. The online gemstone evaluation method of claim 2, and wherein the gemstone evaluation instruments include a gemstone weighing instrument used to weight the gemstones and obtain actual gemstone weight data pertaining to the weight of the gemstones, said actual gemstone weight data being stored in said database, and the remote terminal using said instrument emulation software to simulate weighing said selected gemstone.

5. The online gemstone evaluation method of claim 2, and wherein the gemstone evaluation instruments include a gemstone geometric measuring instrument used to geometric measure the dimensions and angles of the gemstones and obtain actual gemstone geometric measuring image data pertaining to the geometric measurements of the gemstones, said actual gemstone geometric measuring image data being stored in said database, and the remote terminal using said instrument emulation software to visually emulate the geometric measuring instrument by manipulating the geometric measuring image data to examine the dimensions and angles of each facet of said selected gemstone.

6. The online gemstone evaluation method of claim 1, and wherein the gemstone evaluation instruments is a BrillianceeScope light performance instrument used to examine the light performance of the gemstones and obtain actual gemstone light performance image data for the gemstones, said actual gemstone light performance image data being stored in said database, and the remote terminal using said instrument emulation software to emulate the light performance instrument by manipulating the light performance image data for said selected gemstone.

7. The online gemstone evaluation method of claim 1, and wherein the light performance image data includes videos showing the light performance of the gemstones.

8. The online gemstone evaluation method of claim 2, and wherein the gemstone evaluation instruments include an rough cut instrument to obtain images of the diamond in rough form before cutting and polishing to obtain actual gemstone rough cut image data pertaining to the gemstones, said actual gemstone rough cut image data being stored in said database, and the remote terminal using said instrument emulation software to visually emulate the rough cut instrument by manipulating the rough cut image data for said selected gemstone.

9. The online gemstone evaluation method of claim 2, and wherein the gemstone evaluation instruments include a microscope used to obtain actual gemstone microscope image data pertaining to the gemstones, said actual gemstone microscope image data being stored in said database, and the remote terminal using said instrument emulation software to visually emulate the microscope by manipulating the microscope image data for said selected gemstone.

10. The online gemstone evaluation method of claim 2, and wherein the gemstone evaluation instruments include a ray tracing instrument used to shows how light travels through the gemstones and obtain actual gemstone ray tracing image data pertaining to the gemstones, said actual gemstone color image data being stored in said database, and the remote terminal using said instrument emulation software to visually emulate the ray tracing instrument by manipulating the ray tracing image data for said selected gemstone.

11. The online gemstone evaluation method of claim 2, and wherein the gemstones are diamonds and the evaluation instruments include a diamond identification instrument used to identify the diamonds and obtain actual diamond identification measurement image data pertaining to the diamonds, said actual diamond identification measurement image data being stored in said database, and the remote terminal using said instrument emulation software to visually emulate the diamond identification measurement instrument by manipulating the diamond identification measurement data to zoom in and examine the facet patterns for said selected gemstone.

12. The online gemstone evaluation method of claim 1, and wherein said website is linked to a data delivery system, such as an internet or other data carrier, said specifically selected portions of the actual gemstone image data for the selected gemstone being stored on an associated memory of the remote terminal.

13. The online gemstone evaluation method of claim 1, and wherein the graphic display and corresponding processor have an associated printer, and said specifically selected portions of the actual gemstone image data are printable to said associated printer.

14. The online gemstone evaluation method of claim 2, and wherein the actual gemstone image data stored on said database includes picture data, light return spectral response data and images, and gemstone dimension data.

15. The online gemstone evaluation method of claim 1, and wherein the gemstone evaluation instrument use a measurement process to obtain actual gemstone measurement data for the gemstones, and the remote graphic display and corresponding processor using said emulator software and graphic user interface to emulate the actual measurement process on the selected gemstone.

16. The online gemstone evaluation method of claim 1, and wherein inputting the identification number generates an interactive gemstone certificate screen displayed on graphic display of the remote terminal to select a desired instrument emulation to evaluate the selected gemstone.

17. The online gemstone evaluation method of claim 1, and wherein the identification number is assigned to the specific gemstone when the previous evaluation of the specific gemstone is performed to obtain the actual gemstone image data for the specific gemstone.

18. The online gemstone evaluation method of claim 17, and wherein the identification number is input by selecting from a dropdown screen via a mouse of the remote terminal.

19. The online gemstone evaluation method of claim 17, and wherein the identification number is input by entering the identification number via a keyboard of the remote terminal.

20. An online gemstone evaluation system for emulating a gemstone light performance evaluation instrument previously used to evaluate a plurality of gemstones and obtain actual gemstone light performance image data for the gemstones, said online gemstone evaluation system comprising:
  storing means for storing the actual gemstone light performance image data in a database;
  emulation means for emulating the gemstone evaluation instrument using the actual gemstone light performance image data in said database;
  terminal means usable by the user to input an identification number to identify a selected gemstone, manipulate said emulation means, and display light performance images on a graphic display; and,
  means for incorporating said database, emulation means and terminal means to emulate the operation of the gemstone light performance evaluation instrument and controlably display the actual gemstone light performance image data for said selected gemstone on said graphic display.

21. An online gemstone evaluation system of claim 20, and wherein said storing means and emulation means are provided on a global computer network.

22. An online gemstone evaluation system of claim 21, and wherein the user is a prospective consumer of the gemstone.

23. An online gemstone evaluation system of claim 22, and wherein said terminal means is a personal computer.

* * * * *